United States Patent [19]

van Andel

[11] Patent Number: Plant 7,745

[45] Date of Patent: Dec. 10, 1991

[54] CARNATION NAMED STABARSA

[75] Inventor: Jacob van Andel, Aalsmeer, Netherlands

[73] Assignee: Van Staaveren B.V., Aalsmeer, Netherlands

[21] Appl. No.: 541,521

[22] Filed: Jun. 21, 1990

[51] Int. Cl.[5] ..... A01H 5/00

[52] U.S. Cl. ..... Plt./71

[58] Field of Search ..... Plt./70, 71, 72

*Primary Examiner*—Howard J. Locker

*Attorney, Agent, or Firm*—Charles W. Rummler

[57] ABSTRACT

A new and original mini-spray carnation variety particularly distinguished by the unusual light purple coloration of its small sized blossoms, which are produced intermittently during the Spring and Fall blooming seasons. The plant itself is vigorous, strong and upright and obtains a height of about 60 cm.

1 Drawing Sheet

BACKGROUND OF THE NEW PLANT

This new mini-spray carnation cultivar originated as a hybrid seedling developed by me at our nursery in Aalsmeer, Holland by crossing two varieties selected from our collection of carnations maintained for breeding purposes at Aalsmeer. This particular seedling was selected for propagation because of its unusual light purple flower coloration and the overall high quality growth habit of the plant. Asexual propagation of this selected plant was done by means of cuttings under my direction at Aalsmeer and such propagation of this new plant was continued from generation to generation to determine whether the novel characteristics of the selected seedling would be retained from generation to generation and its homogeneity could be assured. This proved to be successful and this new mini-spray carnation variety is now being propagated at Aalsmeer.

DESCRIPTION OF THE DRAWING

My new mini-spray carnation cultivar is illustrated by the accompanying photographic drawing, which shows blooming portions of spray stems with buds and flowers in several stages of development, the color rendition being as nearly true to that herein specified as is reasonably possible to obtain by professional photographic procedures.

DESCRIPTION OF THE NEW PLANT

The following is a detailed description of my new mini-spray carnation variety based upon observation of plants grown in greenhouse as well as outdoors at Aalsmeer and blooming during the current year. The color designations stated herein are according to the R.H.S. Colour Chart published by The Royal Horticultural Society of London, England.

THE PLANT

Origin: Seedling.

Parentage:

*Seed parent.*—D. Barbatus (unpatented).

*Pollen parent.*—Stacherry (unpatented).

Classification:

*Botanic.*—Dianthus Hybrid.

*Commercial.*—Mini-spray Carnation.

Form: Strong, upright bush.

Height: About 60 cm, in average.

Main stem:

*Length.*—In average, about 50 cm.

*Growth.*—Vigorous, upright and fast.

*Branching character.*—Hardly any shoots in the flower stem nodes.

Foliage:

*Number of leaves.*—Varies with the season.

*Leaf size.*—About 150 mm long and 10 mm wide at the fifth node.

*Leaf shape.*—Elliptical and slightly curled.

*Margin type.*—Entire.

*Texture.*—Leathery.

*Color.*—Both upper and under side are dark green.

THE BUD

Size: Small.

*Diameter.*—Averaging about 8 mm.

*Length.*—Averaging about 20 mm.

Shape: Cylindrical.

Calyx:

*Shape.*—Cylindrical.

*Size.*—Averaging about 10 mm in width and 20 mm in length.

*Splitting.*—The calyx does not split.

*Aspect.*—Smooth.

Flower stem:

*Character.*—Erect.

*Color.*—Dark green.

*Length.*—Averaging about 50 cm.

THE FLOWER

Blooming habit: Intermittent during blooming seasons.

Size of flower: Small.

*Diameter.*—Averaging about 30 mm.

*Depth.*—Averaging about 10 mm.

Borne: In a cluster.

Shape:

*When first opening.*—Flat.

*When mature.*—High centered.

Petalage:

*Number of petals.*—Relatively few.

*Texture.*—Soft.

*Appearance.*—Velvety.

*Color.*—Both outer petals and inside petals: Body: 76D with stripes and flecks of 75C and 75D. Base: White. Reverse side: 76D with stripes and flecks and 75C and 75D.

Flower stem:

*Length.*—Averaging about 50 cm.

*Color.*—Dark green.

*Character.*—Strong and upright.

Discoloration:

*After full bloom.*—Color turns to 78C.

Persistence: The flowers hang on and dry.

Disease resistance: Resistant to *Fusarium oxysporum.*

Lasting quality: Averaging about 14 days as a cut flower and 21 days on the plant.

REPRODUCTIVE ORGANS

Stamens:

Number: Arrangement: Rudimental.

*Anthers.*—Size: Small. Color: Light brown.

*Filaments.*—Length, from 1 to 8 mm. Color: White.

Pistils:

*Number.*—Very few.

*Styles.*—Length: About 20 mm. Color: White.

Stigmas:

*Color.*—White.

I claim:

1. The new and distinctive carnation plant, substantially as herein shown and described, particularly characterized by the light purple coloration of its flowers, its vigorous and rapid growth habit and the intermittent production of flowers on strong, upright stem, during normal blooming periods.

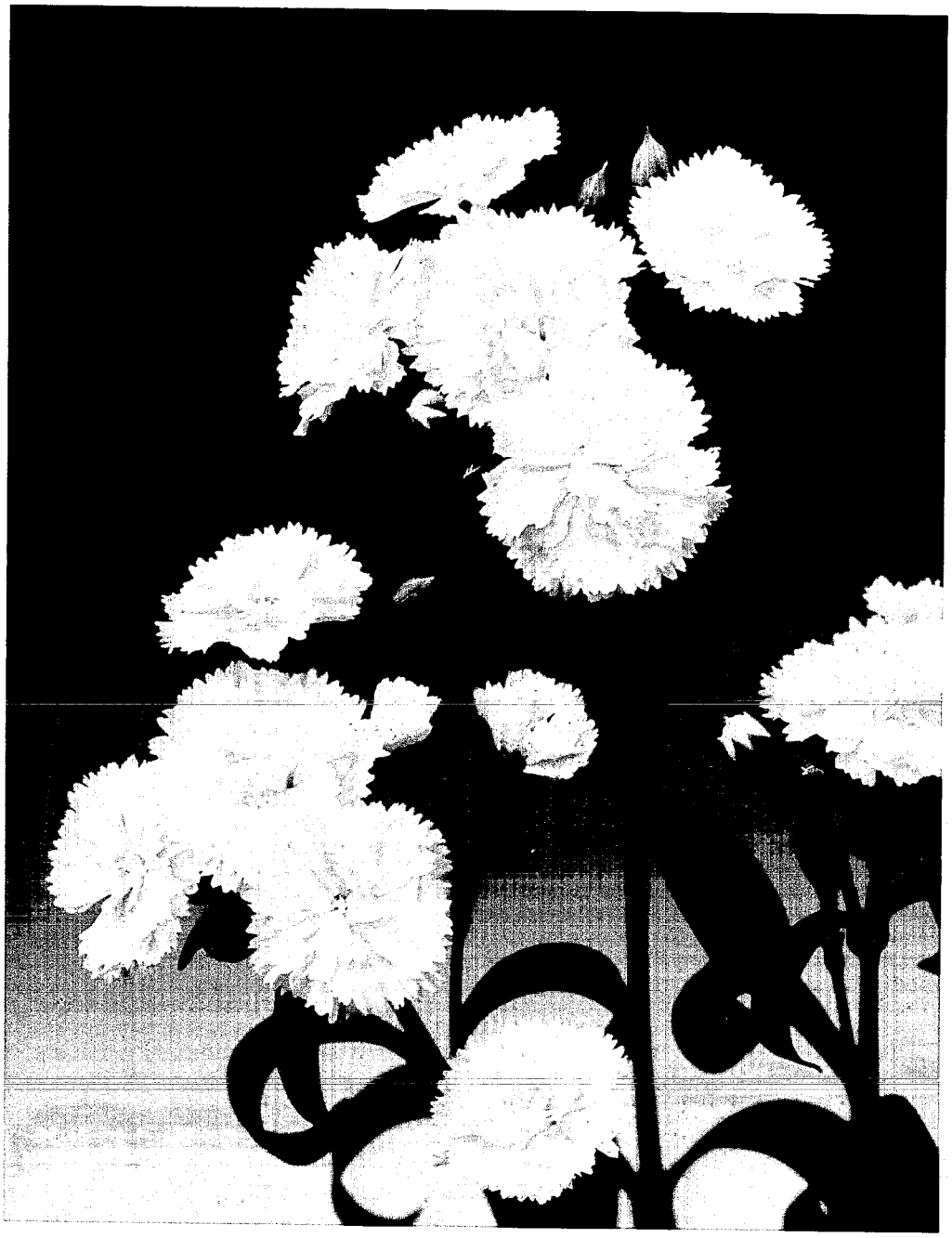

* * * * *